US Patent [19] Masuda

[11] 4,414,323
[45] Nov. 8, 1983

[54] METHOD FOR MEASURING TRACE ENZYME

[75] Inventor: Nobuhito Masuda, Minami-ashigara, Japan

[73] Assignee: Fuji Photo Film Co., Ltd., Kanagawa, Japan

[21] Appl. No.: 298,813

[22] Filed: Sep. 2, 1981

[30] Foreign Application Priority Data

Sep. 2, 1980 [JP] Japan ................................ 55-120601

[51] Int. Cl.³ ..................... G01N 33/52; G01N 33/54; G01N 33/58
[52] U.S. Cl. ....................................... 435/7; 430/537; 430/631; 435/4; 436/805
[58] Field of Search .................. 23/230 B, 915; 424/8, 424/12; 435/7, 4; 430/537, 631

[56] References Cited

U.S. PATENT DOCUMENTS

| 4,151,043 | 4/1979 | Bhattacharyya | 435/4 |
| 4,331,444 | 5/1982 | Mihara | 23/230 B |
| 4,337,063 | 6/1982 | Nihara | 23/230 B |
| 4,337,065 | 6/1982 | Hiratsuka | 23/230 B |

Primary Examiner—Sidney Marantz
Attorney, Agent, or Firm—Sughrue, Mion, Zinn, Macpeak and Seas

[57] ABSTRACT

In a photochemical measurement method of a trace enzyme which comprises: using a synthetic substrate bringing either the reaction product formed by enzyme reaction or the unreacted synthetic substrate into contact with silver halide, developing the same, and measuring optical density of the formed silver image and/or colored dye, the synthetic substrate comprises at least one structure (A) which is specifically contacted with an enzyme to be measured and at least one photographically fogging agent structure (B) in the molecule thereof.

6 Claims, No Drawings

METHOD FOR MEASURING TRACE ENZYME

BACKGROUND OF THE INVENTION

1. Field of the Invention

This invention relates to a method for measurement of a trace enzyme, more particularly, to a method for photochemical measurement of a trace enzyme.

2. Development of the Invention

Various methods have heretofore been developed for measuring the activity of a trace enzyme. For example, there are: a turbidimetric method wherein the decrease in turbidity caused by an enzyme reaction is traced using a suspension of a high molecular weight substrate; an absorptiometric method wherein a high molecular weight substrate is decomposed or cleaved by an enzyme and, after precipitating and removing undecomposed substrate, soluble component is determined by an absorbance measurement; a method wherein a dye or fluorescent substance is previously bound to a high molecular weight substrate, an enzymatic reaction is effected to decrease the molecular weight of the dye or fluorescent substance, and the fractionated dye or fluorescent substance of lower molecular weight is measured; and a method of quantitative assay wherein, using a substrate which is designed to change in absorption spectrum, one forms a color or forms a fluorescent substance, based on a splitting-off or change in a part of the substrate after an enzymatic reaction, and the resulting absorbancy or fluorescent intensity is measured, etc. (SEIKAGAKU JIKKEN KOZA (lectures on Biochemical Experiments), vol. 5, subtitled "Study on Enzymes", edited by the Biochemical Association, Japan, published by Tokyo Kagaku Dojin, 1975).

Most of these methods, however, quantitatively determine an amount of enzyme on the order of $\mu$g/ml. Even utilizing a type of substrate releasing a fluorescent substance (e.g., derivatives of coumarin, umbelliferone, etc.), which is recognized to be most sensitive among these conventional methods, it is only possible to measure an enzyme quantity on the order of ng/ml.

Therefore, in activity measurements of trace enzymes labelled in accordance with enzyme immunoassay, the development of more stable and more highly sensitive enzyme activity measurement methods has been desired.

Further, since the enzymes as biocomponents in blood, body fluids, urine and in tissues in the living body such as various organs, the brain, etc. mostly are present in a very small quantity, except for certain enzymes (amylase, GOT, GPT, etc.) which exist in a large amount, such enzymes cannot be determined by conventional measurement methods. Therefore, a radioimmunoassay (hereafter merely "RIA") which is an immunological measurement method using a radioactive isotope has recently been introduced. The principle of RIA is described in, for example, Kumahara and Shizume, RADIOIMMUNOASSAY, New Edition, pages 3 to 10 (1977), published by Asakura Publishing Co., Ltd., KISO SEIKAGAKU JIKKENHO (Basic Biochemical Experiments) (6), Biochemical Assay (1967), published by Maruzen Co., Ltd., Tokyo, METHODS IN ENZYMOLOGY, edited by Sidney P. Colowick et al, vols. I, II, III, V and VII, published by Academic Press, New York and The Enzyme, vols. 3, 4 and 5, Paul D. Boyer et al (1971), published by Academic Press, New York.

However, RIA as a quantitative assay for enzymes has disadvantages such as: (1) since it is an immunoassay, there is the possibility that the activity of an enzyme—which is the functional characteristic of the enzyme—will not be actually reflected; (2) there is the possibility that analogous enzymes and precursors having a similar antigenic site might be included in analytical data; and (3) in the case where the enzyme to be measured, for example, such as an enzyme in an antigen or antibody labelled with the enzyme used for the enzyme immunoassay, is bound to other component but not present in the free state, it is difficult to prepare an antibody corresponding to the aforesaid labelled antigen or antibody and design for a method for measurement is practically difficult.

RIA has further disadvantages due to the use of radio-isotopes. That is: (1) potential injury to the person dealing with radiation is a matter of concern; (2) special places and controls are required for storage and waste disposal of the radioactive substances used; (3) the amount of radiation from the radioisotope is reduced with the passage of time due to the half decay of the isotope; and (4) measurement of the count of radioactivity requires expensive devices.

The information obtained by measuring enzyme activity using a specific substrate under given reaction conditions (e.g., concentration of substrate, total volume, reaction pH, reaction temperature, reaction time, ionic strength, salts co-existent, etc.) is generally classified as follows:

(1) The sum of enzyme activities having a catalytic action on the structure of the substrate in the system; or (2) Under the condition at constant enzyme concentration, a degree of inactivation depending upon purity of an enzyme, the presence or absence of inhibitors, intensity of inhibition, denaturation, etc., i.e., measure of specific activity.

Finally, the purpose of measuring the activity of an enzyme as a component in the living body is frequently to obtain mainly information per (1) above and the purpose of activity measurements of enzyme-labelled materials exterior a living body is to obtain mainly information per (1) and (2) above. As is well known, in any case, specific enzyme activity can only be measured by selecting a substrate corresponding to enzyme specificity.

The term "specificity" referred to herein is art-recognized and defines selective reactivity between substances, e.g., of an enzyme with its corresponding substrate.

SUMMARY OF THE INVENTION

As a result of research on assays for a trace enzyme, we have discovered a method for measurement of enzyme activity having an extremely high sensitivity, by the use of a substrate specifically possessed by an enzyme and the photochemically fogging function of a fogging agent in combination.

One object of this invention is therefore to provide a method for measurement of enzyme activity of an extremely high sensitivity by the use of the substrate specificity of an enzyme and the photochemically fogging function of a fogging agent in combination.

Another object of this invention is to provide a novel method for measurement of enzyme activity in the measurement of the activity of a labelled enzyme at the measurement step in enzyme immunoassay.

The term "trace" used herein refers to a minute quantity, generally in the order of μg/ml or less, while not limited thereto.

The measurement method of this invention provides not only a very high sensitivity but also is effectively applied to the situation where an enzyme is in the form of a conjugate or complex thereof with other organic materials (e.g., polymers, latexes, microcapsules, membranes); bacteria; microorganisms; components in the living body (e.g., hormones, peptides, proteins, lipoproteins, sugar proteins, glucosides, lipids, etc.), toxic substances; drugs; antibiotics, etc.).

The method for measurement of enzyme activity or a quantity of an enzyme according to this method comprises:

using a synthetic substrate comprising at least one fogging agent structure (B) capable of fogging silver halide by contacting with (or adsorbing to) silver halide grains and at least one structure (A) to be specifically contacted with the enzyme to be measured, bringing either the reaction product comprising fogging agent structure (B) formed by the enzyme reaction or the unreacted synthetic substrate into contact with silver halide followed by development, and, measuring the amount of developed silver and/or the amount of colored dye obtained as an optical density.

The term "synthetic substrate" used herein refers to a substrate synthesized in the laboratory as opposed to substrates derived from living tissues and is recognized in the art (see, e.g., Japanese patent application OPI 52691/77; in the specification, OPI number used for identifying a Japanese patent application as a citation refers to an application laid open to public inspection while its examination has not yet been completed). The synthetic substrate used in this invention comprises structure (A) and structure (B) described above.

Structure (A) generally comprises a site to be catalytically affected with an enzyme to be measured (in other words, a site to be catalytically, e.g., cleaved with the enzyme) and a site to be specifically recognized with the enzyme (i.e., recognition site or binding site) and thus specifically contacted with the enzyme.

The enzymatic reaction which occurs in the measurement method of this invention is illustratively shown below.

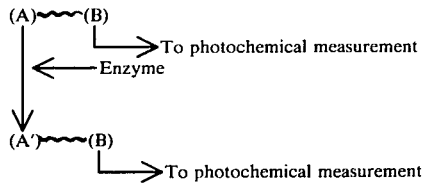

(A): structure (A)
(B): structure (B)
(A'): functionally changed from (A) on contact with enzyme
(A)〜〜〜(B): unreacted synthetic substance
(A')〜〜〜(B): reaction product of enzymatic reaction
〜〜〜: linkage directly linking (A) and (B) or indirectly via linking group (C)

DESCRIPTION OF THE PREFERRED EMBODIMENTS

In the method of this invention, typically, a synthetic substrate containing at least one structure (A) which is specifically contacted with an enzyme to be measured and at least one fogging agent structure (B) are mixed and reacted with a testing sample containing the enzyme to be measured in an appropriate buffer solution, the formed reaction product containing the fogging agent structure (B) is separated from the unreacted synthetic substrate in the manner described hereinafter, and one of them is spotted on a layer containing silver halide. In this case, the reaction mixture may also be directly spotted onto a silver halide-containing sheet itself having a separation means such as a separation layer, etc.

Then, development follows and the resulting density of the developed silver and/or colored dye at the spotted area is measured to determine enzyme activity of the testing sample. Also when the value of the enzyme activity per amount of an enzyme (specific activity) is constant, the amount of the enzyme to be measured can be determined from the optical density of the developed silver or colored dye by reference to corresponding values on a calibration curve or, in the case of calibrating changes of specific activity, etc., the specific activity can be calculated using the same calibration curve and comparing to the black density and/or the colored dye density on the same enzyme quantity basis. This is because the optical density of the thus formed blackened areas and/or colored dye is proportional to the amount of fogging agent adsorbed on silver halide, which is in turn proportional to the amount of the enzyme to be measured.

The method of this invention can apply not only to enzymes in the living body but also to enzymes, e.g., present in soil, culture solutions, culture media, etc., enzymes recovered from a living body or the aforesaid materials, enzymes immobilized to various soluble or insoluble carriers, and enzymes contained in the enzyme-labelled antigens or antibodies.

Fogging agents which constitute the fogging structure (B) in the synthetic substrate used in this invention, i.e., substances which possess a function or capability of fogging silver halide, are generally known as chemical sensitizers in the photographic art, and are exemplified by sulfur-containing compounds, reducible compounds, metal complexes, etc. Details on these fogging agents are described in T. H. James, THE THEORY OF THE PHOTOGRAPHIC PROCESS, 4th ed., pp. 393-395 (1977), published by MacMillan Co., Ltd.

More specifically, useful fogging agents are:

1. Compounds containing a cyclic or acyclic thiocarbonyl group (e.g., thioureas, dithiocarbamates, trithiocarbonates, dithioesters, thioamides, rhodanines, thiohydantoins, thiosemicarbazides, or derivatives thereof)

2. Compounds containing a cyclic or acyclic thio ether group (e.g., sulfides, disulfides, polysulfides, etc.)

3. Other sulfur-containing compounds (e.g., thiosulfates, thiophosphates, and compounds derived therefrom)

4. Nitrogen-containing reducible compounds (e.g., hydrazines, hydrazones, amines, polyamines, cyclic amines, hydroxylamines, quaternary ammonium salt derivatives, etc.)

5. Reducible compounds (e.g., aldehydes, sulfinic acids, enediols, metal hydride compounds, alkyl metals, aromatic compounds in dihydro form, active methylene compounds, etc.)

6. Metal complexes (e.g., four-coordinate Ni (II) or Fe (II) complexes having sulfur as a ligand, etc.)

7. Acetylene compounds

8. Others (Phosphonium salts, etc.)

The order of preference in these fogging agents is, in succession, 4, 5 and 6 as the most preferred group, and then 1, 2, 7 and 3 as the second most preferred.

Specific examples of fogging agents which are particularly preferably employed include:

4-a. Hydrazine compounds of formula (I):

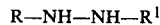

R—NH—NH—R¹   (I)

wherein R and R¹ each represents an alkyl group, an aryl group, a heterocyclic nucleus, an acyl group, a sulfonyl group, an alkoxycarbonyl group, and a derivative thereof (R and R' may be the same or different).

For example, there are hydrazine compounds such as 4-(2-formylhydrazinyl)phenylisothiocyanate, described in, e.g., Japanese patent application OPI 81120/78, German Pat. No. 1,597,493, Japanese Patent Publication 22515/71, U.S. Pat. Nos. 2,663,732, 2,618,656, 2,563,785, 2,588,982, 2,604,400, 2,675,318, 2,685,514 and 3,227,552, British Pat. No. 1,269,640, French Pat. Nos. 2,148,902 U.S. Pat. Nos. 4,080,207, 4,030,925 and 4,031,127, Research Disclosure No. 17626 (1978, No. 176), German patent application OLS No. 2,719,371, Japanese patent applications OPI 74729/79, 52050/80 and 74536/80. Japanese patent application OPI 125062/78, etc. and aldehyde compounds described in, e.g., Japanese Patent Application OPI 9678/72, Japanese Patent Publications 19452/77 and 20088/74, etc.

5-b. Metal hydride compounds

There are metal hydride compounds described in, e.g., Japanese patent publication 28065/70, U.S. Pat. Nos. 3,951,665 and 3,804,632, British Patent 821,251, etc.

5-c. Dihydro compounds

In this invention, dihydro compounds described in, e.g., U.S. Pat. No. 3,951,656, Belgian Pat. No. 708,563, German Pat. Nos. 1,572,125 and 2,104,161, British Pat. Nos. 1,282,084 and 1,308,753, German Patent Application OLS No. 1,572,140, etc. can also be employed.

9. Acetylene compounds represented by formula (IV):

R—C≡CH   (IV)

wherein R is the same as defined for R¹, R² or R³ in 4-a and 4-b.

In this invention, acetylene compounds described in, e.g., German patent application OLS No. 2,655,870, including as a representative a compound of formula:

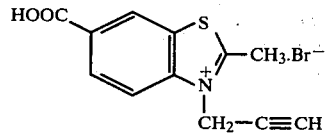

4-b. Hydrazone compounds of formula (II):

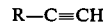

R¹—NH—N=C⟨R²/R³   (II)

wherein R¹, R² and R³ each represents an alkyl group, an aryl group, a hetero ring, an acyl group, a sulfonyl group, an alkoxycarbonyl group and a derivative thereof.

There are hydrazone compounds such as 2-(2-isopropylidenehydrazino)phenyl isothiocyanate, etc., described in, e.g., U.S. Pat. Nos. 3,227,552 and 3,615,615, Japanese Patent Application OPI 3426/77, Japanese Patent Publication 1416/76, etc.

5-a. Aldehyde compounds of formula (III):

R—CHO   (III)

wherein R is the same as defined for R¹, R² and R³, e.g., compounds of the following formula:

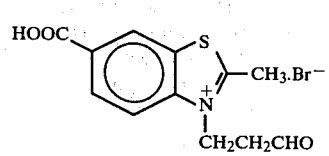

Enzymes which are to be measured in accordance with this invention are known, depending upon mode of contact in enzyme reaction, as hydrolase type enzymes (e.g., protease, nuclease, glycogenase, esterase, lipase, etc.) which cleaves bonds in substrate molecules, a peptide bond, ester bond, phosphate bond, glucoside bond, acid amide bond, etc., by the addition of a water molecule; so-called eliminase and transferase type enzymes which release a specific functional group contained in substrates or transfer it to another substrate; electron transfer type enzymes which contribute to the transfer of oxygen to the substrates; redox type enzymes which contribute to the redox reaction of the substrates, etc.

Representative examples of enzymes which are objectives to be assayed in accordance with the method of this invention include proteases such as trypsin, plasmin, kallikrein, thrombin, chymotrypsin, urokinase, catepsin, streptomyces alkali protease, papain, ficin, bromelain, renin, collagenase, erastase, etc.; peptidases such as leucine aminopeptidase, aminopeptidase, acylaminopepsidase, carboxypeptidase, dipeptidyl peptidase, etc.; nucleases e.g., ribonuclease A, ribonuclease T₁, deoxyribonuclease A₁, endonuclease, etc.; glycogenase including lyase type enzymes e.g., amylase, lysozyme, glucosidase, galactosidase, mannosidase, phosphorylase, glucanase, hyaluronidase, chondroitinase, arginic acid lyase, etc.; lipases, e.g., lipase, phospholipase, etc.; transferase, e.g., transcarbamylase, aminotransferase, acyltransferase, phosphotransferase, etc.; lyases, e.g., carboxylase, hydrolyase, ammonialyase, etc.

Such enzymes are described in detail, for example, in ENZYME, edited by Masaru Funatsu, published by Kodansha Publishing Co., Ltd., 1977, DATABOOK OF BIOCHEMISTRY, first & second separate volumes, edited by Biochemical Association, Japan, published by Tokyo Kagaku Dojin, 1979 & 1980, The Enzyme, vols. III, IV and V, Paul. D., Boyer et al., 1971, published by Academic Press, etc.

In the practice of the method of this invention, it is necessary for assaying the activity of an enzyme, to react the synthetic substrate and the enzyme to be assayed and to bring either the reaction product containing the fogging structure formed as a result of the enzyme reaction or the unreacted synthetic substrate into contact with a silver halide.

In the above-described enzyme reaction mode, either the reaction product formed by the enzyme reaction or the unreacted synthetic substrate can be detected since both the components differ from each other in chemical and physical properties. For example, both components can be separated from each other, utilizing their difference in adsorptive property to silver halide or using another proper separation method (for example, ion exchange chromatography, high speed liquid chromatography, TLC, salting out, centrifugal separation, co-precipitation with a polymer, decantation, ultrafiltration, affinity chromatography, immune reaction, use of an adsorbent such as activated carbon, etc.). The method of this invention can be applied to any types of enzymes described above and details thereof are described in DATABOOK OF BIOCHEMISTRY, Chapter 10, second separate volume, edited by Biochemical Association, Japan, published by Tokyo Kagaku Dojin, 1979. Of these enzymes, hydrolase type enzymes can extremely easily be assayed in accordance with the method of this invention.

The method of this invention can be utilized for the activity measurement and determination of enzymes having the above described contact modes in enzymes labelled to antigens or antibodies as are used in enzyme immunoassay. Enzyme immunoassay is a method of detecting and determining at high sensitivity trace components in the living body or trace drugs, utilizing a specific binding mode of an antigen-antibody reaction and the catalytic action of enzymes in combination. In other words, in enzyme immunoassay, after binding an enzyme to an antigen or antibody, the extent of the antigen-antibody reaction is detected using the enzyme activity as a labelling substance and the amount of the antigen or antibody is determined based thereon. Such measurement systems are generally classified as follows: the case where the antigen and/or antibody is to be measured; the case where an enzyme-labelled antigen (or antibody) is competitive or not competitive with an enzyme-unlabelled antibody (or antigen), and the case where a labelled antigen (or antibody) is competitive with an unlabelled antibody (or antigen), the antigen-bound antibody is separated or not separated from the unbound antigen or antibody prior to measurement. Of these methods, typical methods include (1) a solid phase method, (2) a double antibody method, (3) a homogenous system enzyme immunoassay, and (4) a sandwich method. Details of these methods are described in, for example, Wisdom, Clin. Chem., vol. 22, 1243 (1976), A. Voller et al. The Enzyme Linked Immunosorbent Assay, published by Flowing Publications, Guerney, Europe (1977); M. J. O'Sullivan et al. Annals of Clinical Biochemistry, vol. 16, 221 (1979), Kiyoshi Miyai, Enzyme Immunoassay, Clinical Test, vol. 22, No. 11, extra edition in 1978, and Eiji Ishikawa, Tadashi Kawai and Kiyoshi Miyai, KOSO MENEKI SOKUTEIHO (Enzyme Immunoassay), published by Igaku Shoin, 1978.

By the application of the method of this invention for activity measurement of an enzyme labelled to an antigen or antibody, the enzyme activity can be assayed at higher sensitivity and with greater safety than with conventional methods, whereby the sensitivity and the accuracy of the immunoassay is enhanced.

Structure (A) used in this invention which is specifically contacted with an enzyme to be measured, generally comprises a contact site for an enzyme, such as a peptide bond (acid amide bond), an ester bond, a phosphate bond or a glucoside bond to hydrolase enzymes, an amino group, a carboxy group, etc. to transferase enzymes; and a recognition site or binding site for the enzyme such as an amino acid residue, sugar, a nucleic acid base, etc. These are more specifically described in, for example, DATABOOK OF BIOCHEMISTRY, first and second separate volumes, edited by Biochemical Association, Japan, published by Tokyo Kagaku Dojin, 1979 & 1980, and The Enzyme, vols III, IV and V, edited by Paul D., Boyer, et al, published by Academic Press, 1971, as substrate structures corresponding to the substrate specificity of an enzyme.

The synthetic substrate used in this invention is composed of at least one of the above described structures (A) corresponding to the substrate specificity of an enzyme and at least one of the above described fogging agent structures (B), which are linked with each other directly or through linking group (C). At the conditions for linking these structures with each other: (1) the enzyme reactivity should not be inhibited by the linking; and (2) the fogging activity should not be lost by the linking.

Linking group (C) contains at least two functional groups in the molecule thereof which are capable of linking (A) and (B) and is exemplified by a group derived from an amino acid (e.g., —NH—CH(R)—CO wherein R is an alkyl group which may be substituted), peptide, polyamino acid, monosaccharide, disaccharide, polysaccharide (oligomer and polymer), nucleic acid base, nucleotide, nucleoside, polynucleoside, polynucleotide, etc. The linking is effected via functional groups on structure (A) (e.g., an amino group, an imino group, a carboxy group, a hydroxy group, a sulfhydryl group, or a group capable of reacting with these groups) and functional groups on fogging agent structure (B) (e.g., an amino group, an imino group, a carboxy group, a hydroxy group, a sulfhydryl group, or a group capable of reacting with these groups, etc.). These functional groups may exist in each structure or may be introduced into each structure by the chemical reaction therewith of a compound containing such a group. Further, these functional groups may be employed singly or in combination.

In general, most of substrates contain functional groups such as an amino group(s), a carboxy group(s), a hydroxy group(s), etc., therein. For example, in proteolytic enzymes their substrates typically contain a hydroxy group(s) in the molecule thereof as a functional group(s) for effecting linking with fogging agent for introducing structure (B) or for effecting such a linking via linking group (C).

On the other hands, as the compound having a group capable of reacting with the aforesaid functional groups, there are following compounds: alkyl chloroformates (e.g., diethyl chloroformate, isobutyl chloroformate, etc.), aldehydes (e.g., formaldehyde, glutaraldehyde, etc.), isocyanates (e.g., xylylene diisocyanate, tolylene diisocyanate, hexamethylene diisocyanate, etc.), thioisocyanates (e.g., xylylene thioisocyanate, etc.), vinyl compounds (e.g., divinyl ketone, methylene bisacrylamide, divinyl sulfone, etc.), active halides (e.g., cyanuric chloride, mucohalogenic acids, nitrophenyl chloride, phenol-2,4-disulfonyl chloride, etc.), active esters (e.g., p-toluenesulfonic acid succinyl ester, etc.), imidazolic acid amides (e.g., carbonyl diimidazole, sulfonyl diimidazole, triimidazolyl phosphate, etc.), pyridinium compounds (e.g., N-carbamoyl pyridinium, N-carbamoyloxypyridinium, etc.), sulfonic acid esters (e.g., alkanesulfonic acid esters, etc.), bismaleimides (e.g., N,N'-(1,3-phenylene)bismaleimide, etc.), diazonium compounds (e.g., bisdiazobenzidine, etc.), epoxy compounds (e.g., bisoxirane, etc.), acid anhydrides, carboxylic acids, ethyleneimines, etc.

Further, for linking structure (A) and structure (B) directly or through the linking group (C), for example, a carboxy group among the aforesaid functional groups of the respective structures is activated by a carbodiimide (e.g., 1-ethyl-3-(3-dimethylaminopropyl)carbodiimide, 1-cyclohexyl-3-(2-morphodinyl-4-ethyl)carbodiimide, N,N'-dicyclohexylcarbodiimide, etc.), an isoxazolium, a pseudo base, an active ester (e.g., benzenesulfonic acid hydroxysuccinimide ester, etc.), an alkyl chloroformate (e.g., isobutyl chloroformate, etc.), etc., and then a linking may be formed between the activated group and the functional group of the other structure to be reacted.

With respect to the manner of a linking made between the functional group of structure (A) having specificity for an enzyme and the functional group of fogging agent structure (B) or between each of the functional groups and the functional group of the linking group (C), there are:
(1) linking by direct reaction of the functional groups with each other,
(2) cross-linking by a compound having two or more active functional groups, and
(3) linking formed by activating one of these functional groups using an activator and introducing the activated group to the other functional group (e.g., an amino group, a sulfhydryl group, etc.).

In the case of using linking group (C) in the reaction of linking the two functional moieties (structure (A) and structure (B)) in this invention, it is preferred that the reaction be performed successively from one side to the other in such a manner that structure (A) is linked to linking group (C) between a functional group on structure (A) and one functional group of linking group (C), and then another functional group of linking group (C) is bonded to a functional group on structure (B).

It is preferred that the respective linking reactions be performed in a molar ratio of the two components in the range of from 1/20 to 20/1, preferably from 1/5 to 5/1, more preferably from 1/2 to 2/1. That is, the molar ratio range applies to (a) the linking of structure (A) and structure (B), (b) the linking of structure (A) and linking group (C) and (c) the linking of structure (B) and linking group (C).

The reactive groups and the reaction methods are described in detail in, e.g., SEIKAGAKU JIKKEN KOZA (Lectures on Biochemical Experiments), vol. 1, entitled "Chemistry of Proteins", vol. 2, entitled "Chemistry of Nucleic Acids", vol. 3 entitled "Chemistry of Lipids" and vol. 4, entitled "Chemistry of Glucosides", all edited by Biochemical Association, Japan, published by Tokyo Kagaku Dojin, 1976; and PEPTIDE SYNTHESIS, by Izumiya et al, published by Maruzen Publishing Co., Ltd., 1975, J. P. Greenstein et al, CHEMISTRY OF THE AMINO ACIDS, vols. I-III 1961, John Wiley & Sons, Inc., New York, etc.

In the case of detecting, in particular, a hydrolase type enzyme in the method of this invention, there can be used an immobilized substrate prepared by binding the aforesaid synthetic substrate to a chromatographic carrier, e.g., a latex, polymer beads, plastic chips, glass beads, dextran gel, starch gel, microcapsules, chromatographic carriers such as ion exchange resins, etc., filter paper or the like.

The hydrolase type enzyme used herein includes, e.g., protease, nuclease, glycogenase, lipase, esterase, etc. and is classified into a so-called endo type wherein the substrate specificity is present at the center of the substrate molecule, and a so-called exo type wherein the substrate specificity is present at the terminal of the substrate molecule, respectively. Contact sites of respective enzymes are described in detail in DATA-BOOK OF BIOCHEMISTRY, first & second volumes, edited by the Biochemical Association, Japan, published by Tokyo Kagaku Dojin, 1979 and 1980, P. D. Boyer, The Enzyme, vols. 3, 4 & 5 (1971) Academic Press.

In the method of this invention, an immobilized substrate described above and a high molecular substrate as will be later described are not very effective for exo-type enzymes as to the contact mode. Further, the immobilized substrate used in this invention must meet the requirement that the bond to be specifically decomposed or cleaved by the enzyme to be measured is disposed or inserted between carrier used for immobilization and the fogging agent structure (B). Further, in the case of immobilizing the synthetic substrate it is necessary to take care not to inhibit the action of the enzyme by steric hindrance and, in many cases, it is desirable to insert a spacer (e.g., linking group (C) as used for producing the synthetic substrate) between the functional group on the carrier and the immobilized substrate. The carrier may be in the form of, for example, a plate, a rod, a granule, a fiber or a coating.

By the use of such an immobilized substrate, a low molecular weight substance containing the fogging agent structure (B) is released in the reaction solution by the enzymatic reaction (hydrolysis), whereby the separation of the fogging agent structure from the unreacted synthetic substrate on the carrier becomes unnecessary or extremely easy.

Further, for the reasons as described above, in the method of this invention, a high molecular weight synthetic substrate to which a number of mols of one fogging agent structure (B) are linked per 1 mol of the high molecular synthetic substrate via structure (A) specifically cleaved or decomposed with an enzyme to be measured can be employed for assaying hydrolase enzymes other than exo-type hydrolases. As the fundamental structure of such a high molecular substrate, there are generally structures where the main chain per se of a polymer consists of a repeat of structure (A) (e.g., as in a natural high molecular substrate such as cellulose for cellulase, soluble starch for amylase, protein for protease, nucleic acid for nuclease, etc.) and fogging agent structure (B) forms a side chain(s) thereof from the main chain of the polymer directly or via linking group (C) and a structure where the main chain of the polymer does not possess structure (A) but fogging agent structures (B) forms side chain(s) from the main chain of the polymer via structure (A) to be cleaved. In any case, the enzyme reaction product containing fogging agent structure (B) having a reduced molecular weight is formed as a result of the enzymatic reaction, which can easily be separated from the unreacted synthetic substrate.

In both the case of using the immobilized synthetic substrate and the case of using the high molecular synthetic substrate, it is preferred in this invention to use the fogging agent structure to be assayed by bringing the same into contact with silver halide as the reaction product which is released or changed to a lower molecular weight as a result of the enzymatic reaction.

According to the method of this invention, a plurality of enzymes contained in a test sample can be discriminatively and/or simultaneously detected. That is, as a specific method for discriminatively assaying two or more enzymes, there is a method wherein a substrate fitting only one kind of enzyme among a plurality of enzymes is used utilizing the specificity of the enzyme, a method wherein a substrate is endowed with the specificity to an enzyme by controlling the reaction conditions (e.g., reaction pH, reaction temperature, ionic strength, etc.), a method wherein the measurement of an enzyme is performed in the presence of inhibitors or inactivators specific to enzymes other than the enzyme to be measured, and a method comprising a combination of these methods.

The term "inhibitor" used herein refers to a material which inhibits the function of the enzyme by a reversible change while the term "inactivator" refers to a material which inhibits and inactivates the function of the enzyme by an irreversible change. The inhibitor and the inactivator to each enzyme are described along with the specificity in DATABOOK OF BIOCHEMISTRY, first and second separate volumes, edited by the Biochemical Association, Japan, published by Tokyo Kagaku Dojin, 197- and 1980, The Enzyme, P. D. Boyer, vols. 3, 4 and 5 (1971), Academic Press, New York, etc.

Further, as practical methods for simultaneously measuring two or more enzymes discriminatively, there are, for example, the methods described below:

(1) A method which comprises measuring the total activities of all enzyme components, with the progress of the reaction, after a certain period of time, using a synthetic substrate having common specificities to two or more enzymes and simultaneously adding an inhibitor or inactivator acting specifically to only one component of the plural enzyme components, and repeating the above procedure in accordance with the number of the enzyme components to thereby determine the activity of the respective enzyme components from the difference between the total activities before the addition of the inhibitor or inactivator and the activities after the addition thereof at each measured time;

(2) A method which comprises performing enzyme reactions using a plurality of synthetic substrates different from each other, each of which corresponds, in unitary relation, to each enzyme in the plural enzymes to be measured and each of which forms fogging agent structure (B)-containing product having a different structure from any other product or products by an enzyme reaction, either each fogging agent structure (B)-containing product or the unreacted synthetic substrate corresponding to each enzyme being separated by an appropriate separation method (e.g., liquid chromatography, etc.) utilizing differences in physicochemical properties between the plural fogging agent structure (B)-containing reaction products and/or plural unreacted synthetic substrates and then being brought into contact with silver halide, whereafter one develops the separated products or synthetic substrates separately by the number of the enzymes and separately measures densities of the developed silvers and/or colored dyes, thereby determining the activity of each enzyme; and, (3) A method comprising a combination of the above described methods, etc.

In any mode of the method of this invention described above, it is convenient to employ, if desired or necessary, such a method that after stopping the enzyme reaction using appropriate conditions to stop the enzyme reaction (e.g., by increasing or decreasing the reaction pH, or by elevating or lowering the reaction temperature, etc.), or, using an enzyme inhibitor or inactivator or a modifier (e.g., urea, guanidine hydrochloride, or a surface active agent having a modifying action such as SDS, etc.) which is also an inactivator in a broad sense, either the reaction product containing fogging agent structure (B) or the unreacted synthetic substrate is brought into contact with silver halide.

Basic means for assaying either the fogging agent structure-containing reaction product formed by the enzyme reaction or the unreacted synthetic substrate by bringing it into contact with silver halide in accordance with this invention include:

(1) A liquid containing the above described component is dropped onto a silver halide photographic emulsion containing unexposed silver halide grains and adsorbed on the grains. The mixture is placed in a transparent cell, and a developer for photographic use is added to the mixture followed by development to blacken the mixture. Thereafter, optical density is measured (contact in solution).

(2) At least one silver halide emulsion layer containing unexposed silver halide grains is formed on a support, and a liquid containing the above described component is dropped onto the emulsion layer to thereby allow the liquid to permeate into the emulsion layer and adsorb onto the silver halide grains in the emulsion layer. Then, the emulsion layer is immersed in a photographic developer as in ordinary development processing to blacken the developed silver, and then optical density blackened at the spotted area is measured (contact onto film).

Among the above described means, means (2) is particularly preferred and is convenient for assaying a plurality of enzymes. That is, a plurality of reaction products containing fogging structures (B) or plural unreacted synthetic substrates are separated from each other, spotted or dropped on the emulsion layer by at least the number of enzymes to be measured, each spot is immersed in a developer to blacken the spot or drop portions, and blackening optical density or the degree thereof is then measured.

For practicing the method of this invention, in a more preferred embodiment, an analysis element used for the method of this invention comprises an auxiliary layer formed under a silver halide-containing layer to increase the amount of spotted test liquid absorbed. The function of the auxiliary layer referred to herein is to accelerate absorption of the spotted test liquid into the layer and increase the uptake of the aforesaid enzyme to be measured, whereby the amount to be adsorbed onto silver halide grains is increased. Such an auxiliary layer is composed of a porous membrane, a filter paper, a fiber, gelatin and/or a polymer and has a thickness of 1 $\mu$m to 100 $\mu$m, preferably 3 $\mu$m to 40 $\mu$m. This auxiliary layer can also contain, in addition to gelatin or a polymer, silver halide or additives for ordinary silver halide light sensitive materials, e.g., an antifoggant, a dye, a surface active agent, colloidal silver, etc.

Gelatin, when used in this invention as a binder for silver halide or in other layers, is ordinary lime-treated gelatin, acid-treated gelatin, enzyme-treated gelatin, a gelatin derivative obtained by chemically modifying gelatin, such as phthalated gelatin, or graft gelatin obtained by graft polymerizing a monomer in the presence of gelatin. Such gelatin may be used alone or as a mixture thereof in an appropriate proportion. As polymers used in this invention, polymers which are liable to swell or dissolve in water are preferred, examples of which include albumin, agar agar, gum arabic, alginic acid, a hydrophilic homopolymer or copolymer of a polymerizable vinyl monomer such as vinyl alcohol, vinyl pyrrolidone, acrylamide, acrylic acid, methacrylic acid, styrenesulfonic acid, styrene, methyl methacrylate, etc., a cellulose compound (e.g., hydroxyethyl cellulose, carboxymethyl cellulose, dextrin, etc.), water soluble starch, etc. If necessary or desired, a hardening agent may be added to the polymer for insolubilizing the polymer.

Specific examples of silver halides employed in this invention include silver chloride, silver chlorobromide, silver bromide, silver iodobromide, silver chloroiodobromide, silver chloroiodide, silver iodide, etc.

These silver halides can be emulsion dispersed or suspended in hydrophilic colloid binder solution or can be supported onto a support without any binder (e.g., a silver halide layer can be directly formed on a support by vacuum deposition, etc.).

Silver halide(s) contained in a photographic emulsion used in the present invention can be prepared in a conventional manner, e.g., by a single jet method, a double jet method, or a combination thereof. Useful preparation methods of silver halide emulsions are described in, e.g., Trivelli and Smith, The Photographic Journal, vol. 79, pp. 330-338 (1939), C. E. K. Mees, The Theory of the Photographic Process, 1966, published by MacMillian, Glafkides, Photographic Chemistry, vol. I, pp. 327-336, published by Fountain Press, etc.

The grain size of silver halide(s) in an emulsion(s) employed in this invention is conventional or smaller. It is thus generally preferred that the average grain diameter be 0.04 to 4 microns (e.g., by measurement of number average by the projected area method). Further, the size distribution of silver halide grains in a silver halide emulsion is as narrow as possible. For this reason, silver halide grains may be formed by a double jet method or a conversion method, a so-called controlled double jet method for forming silver halide grains while controlling the pAg of the silver halide grain-forming mixture.

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) of a photographic element. The developing agents can be incorporated using a suitable solvent or in the form of a dispersion as described in U.S. Pat. No. 2,592,368 or French Pat. No. 1,505,778.

When a light sensitive film containing the developing agent in a coated layer or layers is used, the film is processed, after light exposure, with an ordinary photographic developer and in this case a so called alkali activator, i.e., an ordinary photographic developer composition from which a developing agent component is removed may be used.

In this invention, as a binder for the silver halide emulsion layer coated on a support, ordinary gelatin (i.e., alkali-treated gelatin or acid-treated gelatin) is usually used. Furthermore, the gelatin may be partially or wholly replaced with another film-forming high molecular weight material. As such a high molecular weight material, there are used materials which do not have a harmful influence on the light sensitive silver halide emulsion, such as albumin, agar agar, gum arabic, alginic acid, acylated gelatin (e.g., phthalated gelatin, malonated gelatin, etc.), a homopolymer or a hydrophilic vinyl compound (e.g., vinyl alcohol, vinylpyrrolidone, acrylamide, styrenesulfonic acid, acrylic acid, etc.) or copolymers containing these vinyl compounds, cellulose compounds (e.g., hydroxyethyl cellulose, carboxymethyl cellulose, dextrin, etc.), water-soluble starch, etc. Other layers (e.g., a filter layer, subbing layer, etc.) than the silver halide emulsion layer may contain such a film-forming high molecular weight material as in the silver halide emulsion layer.

The development performed in this invention can be by the following manner. That is, when a silver halide emulsion is formed on a support, a development process as is conventionally used for the development of photographic materials can be used. Also, the photographic development can be performed by spreading, coating, impregnating or spraying a photographic developing composition onto the silver halide emulsion layer formed on the support. Furthermore, when the silver halide emulsion is in the liquid state, photographic development can be performed by mixing the emulsion with a liquid developing composition.

The silver halide emulsion layer contacted with the fogging agent as described above is processed by a conventional photographic processing. A known processing solution can be used in this case. The processing temperature is usually selected from 18° C. to 50° C., but may be lower than 18° C. or higher than 50° C.

With an increase in developing temperature, photographic density increases. Therefore, it is usually preferred to process at a pre-determined constant temperature. However, in place of processing at a constant temperature, a process may be employed wherein changes in photographic density due to changes in developing temperature are substantially prevented by using a neutralizing layer and a temperature compensation polymer layer. For example, the development can be performed on a silver halide emulsion layer formed adjacent a combined layer of an acid polymer layer as described in U.S. Pat. Nos. 4,056,394 and 4,061,496 and Japanese Patent Applications OPI 72622/78.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

As a special aspect of development, a developing method which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in Research Disclosure, No. 169, RD-16928. Such development processing can also be used in combination with silver salt stabilization, e.g., with a thiocyanate(s).

In place of the above described black-and-white development process, a color development as is used in ordinary color photographic process can also be performed. In this case, a coupler is preliminarily dissolved in the developer or incorporated in the silver halide emulsion layer of a light sensitive element (see, for example, T. H. James, The Theory of The Photographic Process, 4th edition, pages 335 to 362, 1977, published by Macmillan Publishing Co., Ltd.).

By color development, areas contacted with the fogging agent give blackening by silver and coloring by a coloring material, and hence, in color development, a higher optical density than blackening by silver alone is obtained. With developed areas obtained by color development, the light absorption due to blackening of silver and coloring due to dye formation can be measured by light of the light absorption wavelength(s) of the dyes.

After development, a stopping solution may be used in this invention and, as the stopping solution, an aqueous solution containing a compound capable of stopping development such as a pH reducing agent (e.g., a mineral acid, an organic acid, etc.) or a mercapto compound can be used. Also, when the fixing solution used is an acid fixing solution, i.e., having a sufficiently low pH for stopping the development, the stopping solution may be omitted.

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

In this invention measurement of the photographic density or color density after development can be sufficiently performed by means of an optical densitometer as is used for measuring the density of conventional photographic images and hence measurement can be performed simply and at a low cost. In the case of measuring optical density, the photographic density or color density can be measured by inserting a proper color filter in an optical path. Usually the photographic density or color density of a light sensitive element which has been finished via conventional photographic processing and dried is measured; however, the photographic density or color density of the light sensitive element immersed in a processing solution may be measured at the end of development, at the end of stopping, or at the end of fixing.

The invention is further illustrated with reference to the following examples, wherein percentage are all by weight unless otherwise indicated.

EXAMPLE 1

A solution of a fogging agent (100 mg) of formula (I):

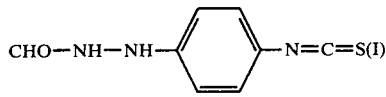

in 5 ml. of DMF was dropwise added to a solution of 126 mg. of glycyl-L-phenylalanineamide in 5 ml. of DMF with stirring while keeping at 4° C. After reacting the mixture for 30 mins. at 4° C. and for further 1 hr. at room temperature, the reaction product was separated and purified by silica gel column chromatography. Thus, the desired product, p-(2-formylhydrazino)benzenethiocarbamylglycyl-L-phenylalanineamide, which is a substrate to α-chymotrypsin, was isolated (120 mg., yield 53%).

This product was dissolved in a 0.05 M tris-hydrochloric acid buffer of pH 8.0, containing 1% of a surface active agent, in a concentration of 10 mg/ml. Sample solutions obtained by dissolving 2 μg/ml, 20 μg/ml and 200 μg/ml of α-chymotrypsin in the same buffer, respectively, were prepared. Then, 1 ml. each of the substrate solution described above was added to 1 ml. of the respective sample solutions. The mixtures were well stirred and maintained at 40° C. After reacting the mixtures for 10 mins., 0.1 mg. of TPCK (tosylamidophenylalanyl chloromethyl ketone) was added to the reaction mixtures, respectively, and 1 ml. each of the reaction mixtures having the respective concentrations of α-chymotrypsin was weighed in a Sephadex C-50 column (50 mmØ × 50 mm) which had previously been equilibrated with a 0.05 M tris-hydrochloric acid buffer of pH 8.0, which column was further washed with 1 ml. of the same buffer. Effluents and washed liquids were combined and the combined liquids were spotted by 25 μl at an area of 5 mmØ onto a film comprising a TAC support having coated thereon unexposed silver halide (Br 70 mol%, AgBrCl, average grain size 0.8 μm) as a single coating layer. As a blank, a solution obtained by treating a mixture of 1 ml. of the aforesaid buffer and 1 ml. of the aforesaid substrate solution according to quite the same procedures was spotted side by side. After allowing to stand for 20 mins., the fogging agent in the solutions was sufficiently adsorbed to silver halide. Thereafter, development was performed with Developer A having the following formulation at 20° C. for 10 mins.

| Developer A | |
|---|---|
| Metol | 3.1 g |
| Sodium sulfite | 45 g |
| Hydroquinone | 12 g |
| Anhydrous sodium carbonate | 67.5 g |
| KBr | 1.9 g |
| Water to make | 1 liter |

Then, fixing, washing with water and drying followed in a conventional manner, and black densities on the thus obtained photographic film were measured with a photographic densitometer made by Fuji Photo Film Co., Ltd.

Results are shown in Table 1.

TABLE 1

| Concentration of α-Chymotrypsin (μg/ml) | Black Density |
|---|---|
| 0 | 0.13 |
| 2 | 1.22 |
| 20 | 1.79 |
| 200 | 2.35 |

EXAMPLE 2

The same procedures as in Example 1 were repeated using the substrate of Example 1 in the same concentration of 10 mg/ml except that sample solutions of 50 ng/ml, 100 ng/ml and 150 ng/ml of α-chymotrypsin were employed, one being a blank of the buffer alone, solutions obtained by dissolving 0.1 mg of TPCK in 1 ml. of each of α-chymotrypsin sample solutions, respectively, were emloyed and sample solutions having the respective concentrations to which no TPCK was added; were employed seven (7) solutions in total were employed.

Results obtained are shown in Table 2.

TABLE 2

| Concentration of α-Chymostrypsin (ng/ml) | Black Density | TPCK (0.1 mg/ml) |
|---|---|---|
| 0 | 0.14 | — |
| 50 | 0.25 | — |
| 100 | 0.50 | — |
| 150 | 0.59 | — |
| 50 | 0.16 | + |
| 100 | 0.15 | + |
| 150 | 0.17 | + |

EXAMPLE 3

The pH of 100 g of a 10% aqueous solution of gelatin (m.w., ca. 100,000) obtained by removing fractions having a molecular weight of smaller than 50,000 was adjusted with 1 N NaOH to 9.0. While thoroughly stirring the solution, 100 ml. of DMF was added thereto. Further, 1 g. of Compound (I) was dissolved in 10 ml. of DMF and the resulting solution was dropwise added slowly to the gelatin solution described above to cause a reaction. After reacting for about 1 hr., the reaction mixture was dialized to flowing water. Then, the unreacted reagent and decomposition products were removed. After freeze-drying, gelatin modified with the fogging agent was obtained.

1 ml. each of a 0.1% 0.05 M tris-hydrochloric acid buffer (pH 8.0) of the gelatin described above were mixed with 1 ml. of papain solutions having various concentrations. The mixtures were subjected to an enzyme reaction at 40° C. for 20 mins. The resulting reaction mixtures were spotted by 25 μl each at an area of 5 mmØ on a film obtained by coating unexposed silver halide emulsion (AgBrCl, Br content 70 mol%, average grain size 0.7μ) on TAC in a thickness of 6 μm and further coating thereon gelatin in a thickness of 1 μm. After allowing to stand for 10 mins. after the spotting, the film was developed with Developer B having a formulation below at 20° C. for 5 mins.

| Developer B | |
|---|---|
| Metol | 2 g |
| Sodium sulfite | 40 g |
| Hydroquinone | 4 g |
| Sodium carbonate | 28 g |
| Potassium bromide | 1 g |
| Water to make | 1 liter |

In a conventional manner, fixing, washing with water and drying were performed and then, the resulting black densities at the spotted portions were measured to determine difference ΔD from the density of the blank.

Results are shown in Table 3.

TABLE 3

| Concentration of Papain (μg/ml) | Difference in Black Density (ΔD) |
|---|---|
| 5 | 0.32 |
| 10 | 0.61 |
| 20 | 0.99 |
| 40 | 1.35 |
| 80 | 1.93 |
| 160 | 2.67 |

EXAMPLE 4

In 5 ml. of DMF, 10 mg. of 4-aminophenyl-β-D-galactopyranoside obtained by catalytically reducing commercially available 4-nitrophenyl-β-D-galactopyranoside was dissolved. A solution of 10 mg. of Compound (I) described above in 5 ml. of DMF was gradually added to the resulting solution at room temperature with stirring to cause a reaction. After reacting for 1 hr. at room temperature, the desired compound (II) was obtained using a silica gel column (chloroform/methanol=8:2 v/v).

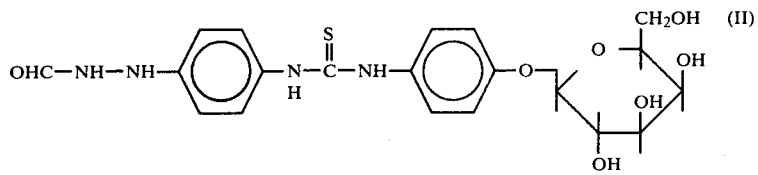

It was confirmed by TLC and UV and visible absorption spectra that this compound was hydrolyzed with β-D-galactosidase (made by Sigma Co., Ltd.) to release a compound:

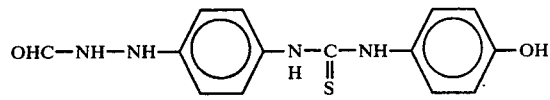

Next, using β-D-galactosidase obtained from E. coli and anti-α-fetoprotein rabbit IgG, an IgG-β-D-galactosidase conjugate was prepared using N,N'-o-phenylenedimaleimide. Further, anti-α-fetoprotein rabbit antibody was immobilized to glass beads having introduced therein amino groups, via glutaraldehyde, to prepare glass beads having immobilized thereto the anti-α-fetoprotein antibody (details are described in KOSO MENEKI SOKUTEIHO (Enzyme Immunoassay), edited by Eiji Ishikawa, et al., published by Igaku Shoin, 1978).

Using these anti-α-fetoprotein rabbit IgG-β-D-galactosidase, anti-α-fetoprotein rabbit IgG-immobilized glass beads (hereafter simply referred to as "glass beads") and Compound (II) described above, a calibration curve with standard α-fetoprotein solutions was prepared in accordance with the procedure described below.

In small test tubes in which a 0.1 M sodium phosphate buffer solution of pH 7.3 containing 0.15 M NaCl and 0.5% bovine serum albumin (Liquid A) was separately weighed by 0.4 ml. each, 0.1 ml. of standard α-fetoprotein solutions having various concentrations (5 to 160 ng/ml) prepared using Liquid A and 20 μl of horse serum were further weighed, respectively. Then a portion of the aforesaid glass beads having the antibody fixed thereto was added to the test tubes, respectively, and the mixtures were allowed to stand for 2 hrs. at 37° C. Thereafter, the reaction liquids were removed using an aspirator, and 1 ml. of a 0.01 M sodium phosphate buffer solution (pH 7.5) containing 0.1 M NaCl and 1 mM MgCl₂ and 0.1% BSA (Liquid B) was added to the residues to wash the same twice. After washing, 0.2 ml. of an anti-α-fetoprotein antibody-β-D-galactosidase conjugate prepared using Liquid B was added and the mixtures were again allowed to stand for 2 hrs. at 37° C. Dilution of the conjugate was performed in such a manner that 160 ng/ml of standard α-fetoprotein indicated black density after development described below of 2.0 to 2.5. Then, after the reaction liquids were removed, 1 ml. of Liquid B was again added to the residues to wash them twice. Then, 0.5 ml. of a 0.1% solution of Compound (II) in Liquid B was added and the mixtures were allowed to stand for 1 hr. at 37° C. Each of the reaction liquids was separately passed through a silica gel column of 3 mmØ×15 mm (chloroform-methanol) to isolate the reaction product:

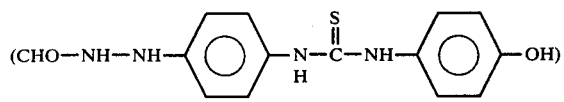

After removing the solvent by distillation, the residues were dissolved in 0.2 ml. of Liquid B, respectively. Thereafter, detection was performed using the film having coated thereon silver halide as in Example 2.

Black densities obtained with the respective standard solutions are shown in Table 4 below.

TABLE 4

| Concentration of Standard Solution (ng/ml) | Black Density |
| --- | --- |
| 0 | 0.21 |
| 5 | 0.53 |
| 10 | 0.85 |
| 20 | 1.20 |
| 40 | 1.55 |
| 80 | 1.92 |
| 160 | 2.18 |

EXAMPLE 5

Instead of Compound (I), 20 mg. of Compound (III) having the following formula:

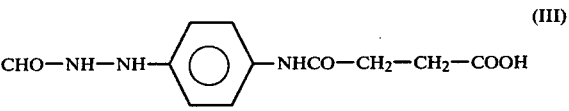

was dissolved in 5 ml. of DMF. Then, after forming a mixed acid anhydride, which was active at −15° to 20° C., using 15 μl. of an activator, isobutyl chloroformate, the above solution was dropwise added to a solution of 15 mg. of glycylphenylalanine ethyl ester in 5 ml. of DMF at 0° C. while stirring to cause a reaction. After reacting at 0° C. for 10 mins. and at room temperature for 1 hr., the reaction mixture was isolated and purified by means of silica gel column chromatography. Even when using this compound, it was possible to assay chymotrypsin in accordance with the same procedures as in Example 1.

While the invention has been described in detail and with reference to specific embodiments thereof, it will be apparent from one skilled in the art that various changes and modifications can be made therein without departing from the spirit and scope thereof.

What is claimed is:

1. A method for assaying a sample for enzyme activity and/or a quantity of an enzyme comprising:
   (a) providing a synthetic substrate comprising at least one structure (A) catalytically affected by the enzyme being assayed and at least one photographically fogging agent structure (B), said structures (A) and (B) being found in the molecular structure of the synthetic substrate;

(b) contacting the sample with the provided synthetic substrate so as to bring about a chemical reaction by said enzyme;
(c) contacting either the reaction product resulting from (b) or the excess unreacted synthetic substrate also resulting from (b) with silver halide;
(d) photographically developing either product resulting from (c); and
(e) measuring the optical density of the silver image and/or the colored dye resulting from (d).

2. The method of claim 1 wherein said enzyme to be assayed is a proteinase, a peptidase, a nuclease, a glycogenase or a lipase.

3. The method of claim 1 wherein said enzyme to be assayed is a proteinase, a nuclease, a glycogenase or a lipase, and said synthetic substrate is linked to an insoluble carrier.

4. The method of claim 1 wherein said enzyme to be assayed is a proteinase, a nuclease or a glycogenase, and said synthetic substrate is a high molecular weight substance comprising at least two of said structure (A) and at least two of said structure (B).

5. The method of claim 1 wherein a plurality of enzyme activities in a system containing at least two enzymes are determined individually in a scheme involving selectively inhibiting or inactivating individual enzymes one at a time.

6. The method of claim 1, 2, 3, 4 or 5 wherein said enzyme to be assayed is an enzyme labelling an antigen or antibody.

* * * * *